United States Patent [19]
Maxwell

[11] Patent Number: 5,603,692
[45] Date of Patent: Feb. 18, 1997

[54] DROP FOOT SPLINT

[76] Inventor: Richard H. Maxwell, 301 N. Broad St., Grove City, Pa. 16127

[21] Appl. No.: 634,837

[22] Filed: Apr. 19, 1996

[51] Int. Cl.⁶ ............................................. A61F 5/00
[52] U.S. Cl. ........................ 602/28; 128/882; 602/16; 602/23; 5/650; 5/651
[58] Field of Search ........................ 602/5, 12, 16, 602/23, 27–29; 5/624, 648, 650, 651; 128/882, 892

[56] References Cited

U.S. PATENT DOCUMENTS

| 3,345,654 | 10/1967 | Noble . | |
| 3,511,233 | 9/1968 | Holy, Jr. | 128/892 |
| 3,523,526 | 8/1970 | Phelps | 602/29 |
| 3,976,059 | 8/1976 | Lonardo . | |
| 4,323,080 | 4/1982 | Melhart | 128/882 X |
| 5,020,523 | 6/1991 | Bodine | 128/882 X |
| 5,042,508 | 8/1991 | Richard | 128/882 |
| 5,088,479 | 2/1992 | Detoro | 602/27 |
| 5,143,058 | 9/1992 | Luber et al. | 602/28 |
| 5,154,695 | 10/1992 | Farris et al. . | |
| 5,224,925 | 7/1993 | Varn | 602/28 |
| 5,267,949 | 12/1993 | De La Torre et al. | 602/23 X |
| 5,298,013 | 3/1994 | Lonardo . | |
| 5,367,789 | 11/1994 | Lamont | 128/892 X |
| 5,372,576 | 12/1994 | Hicks | 128/882 X |
| 5,449,339 | 9/1995 | Drennan | 128/882 X |
| 5,460,600 | 10/1995 | Bieling | 128/882 X |
| 5,542,912 | 8/1996 | Hess | 128/882 X |

Primary Examiner—Linda C. Dvorak
Attorney, Agent, or Firm—Harpman & Harpman

[57] ABSTRACT

A foot drop leg splint used to stabilize a patient's foot who suffers from drop foot when at rest. The splint has a rigid support frame with a contoured foam insert with removable straps to hold the splint on the patient. An adjustable rotational restraint is selectively deployed from the splint to prevent axial rotation of the leg and foot when required.

4 Claims, 3 Drawing Sheets

DROP FOOT SPLINT

BACKGROUND OF THE INVENTION

1. Technical Field

This device relates to therapeutic appliances that are used to hold and immobilize a patient's foot and lower leg suffering from a condition known as drop foot in which the angle between the sole of the foot and the axis of the leg is abnormally obtuse when the muscles are relaxed.

2. Description of Prior Art

Prior art devices of this type have provided a number of different therapeutic leg and foot structures that are secured to the patient's lower leg and foot holding them in the desired position. The devices are of generally two types, the first being a contoured rigid L-shaped member with overlapping padded straps and flaps that define the stabilization portion of the leg and foot, see for example U.S. Pat. Nos. 3,976,059, 5,298,013, 3,345,654 and 5,154,695.

A second group of standard leg and foot splints are characterized by a rigid L-shaped support with a contoured foam insert to delineate the correct position of the foot and leg within to which applicant's invention is derived from.

SUMMARY OF THE INVENTION

A foot drop splint having a rigid L-shaped non-contoured support base with a contoured foam insert supporting the lower leg and foot having a heel recess with detachable engagement straps removably secured thereto. A pair of deployable rotation stabilization outriggers are pivotally secured to the rigid support base adjacent the L-shaped transition point below the contoured leg and heel defining foam insert support.

DESCRIPTION OF THE PREFERRED EMBODIMENT

Figure 1:
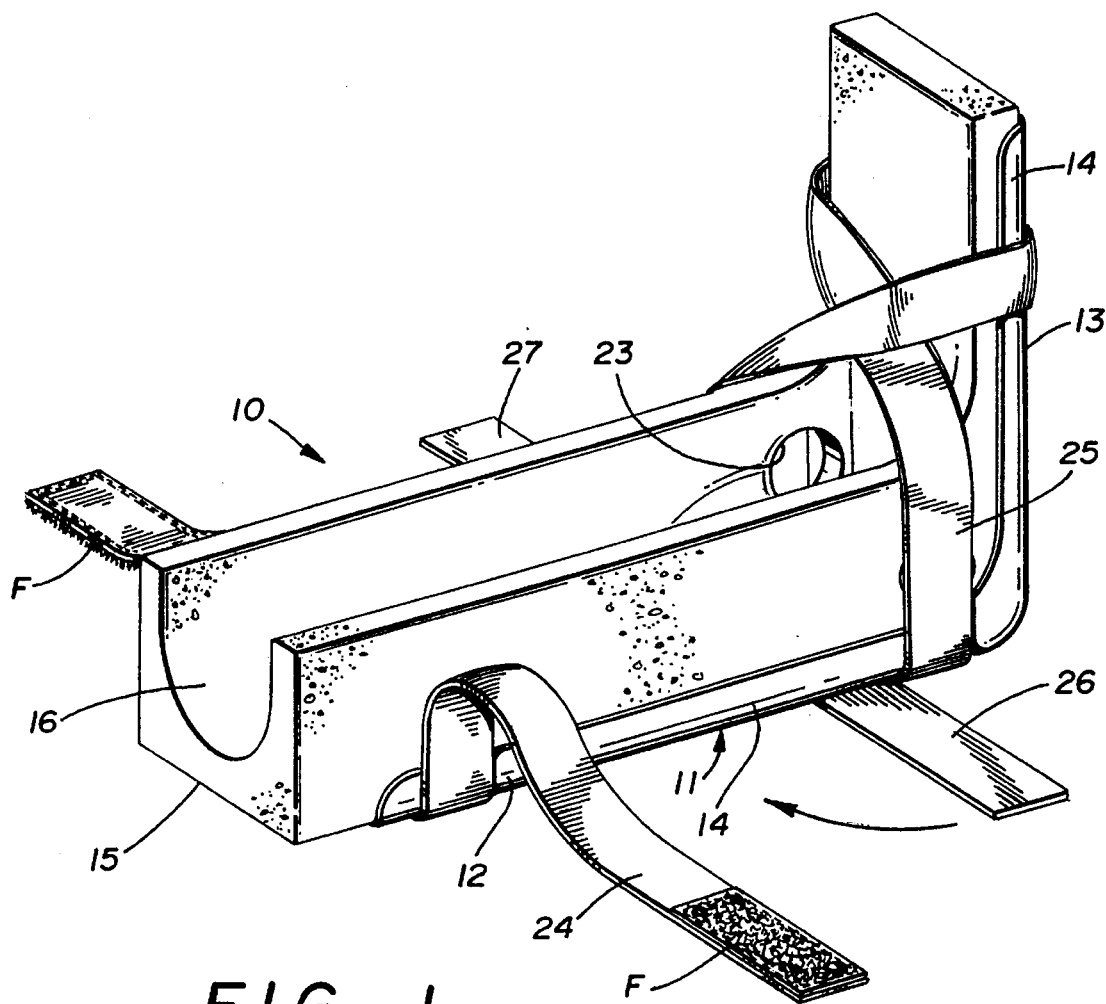
FIG. 1 is a perspective top, front and side view of the foot splint of the invention with stabilizers deployed as in use.
Figure 2:
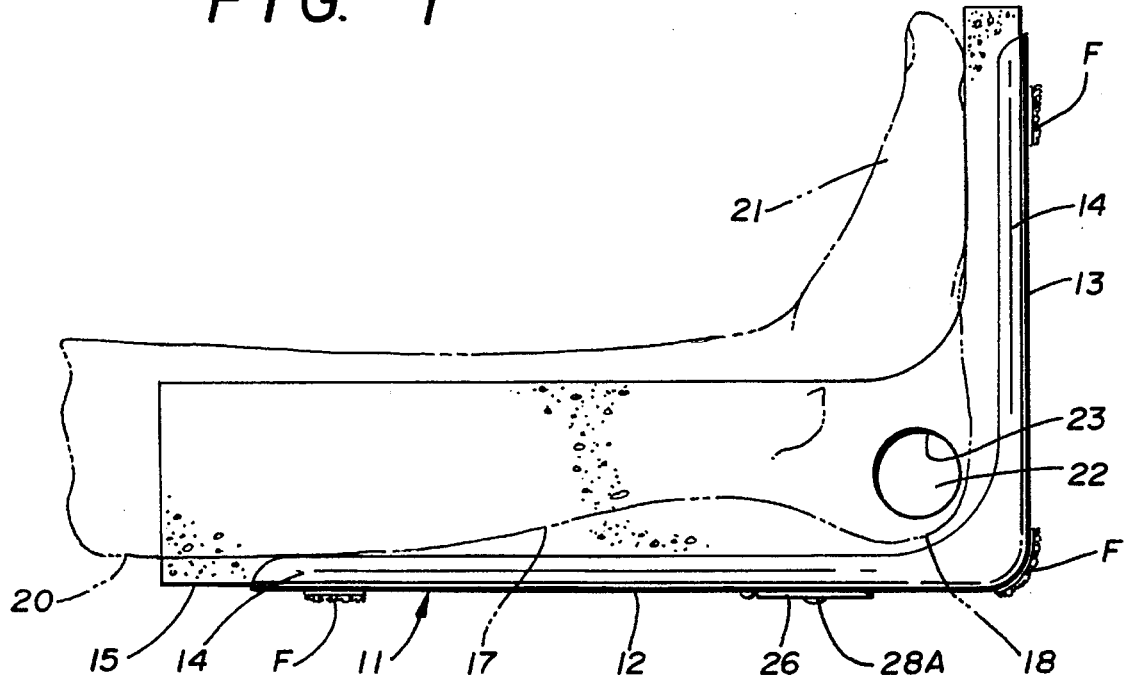
FIG. 2 is a side elevational view thereof with a patient's lower leg and foot illustrated in broken lines positioned therein.

Referring to FIGS. 1 and 2 of the drawings, a foot drop splint 10 can be seen having a rigid L-shaped base 11 with a leg and heel support portion 12 and a foot support portion at 15. The base 11 has contoured upstanding flanges 14 along its parallel perimeter edges defining a mounting area therebetween. A synthetic foam resin support insert 15 is positioned within the mounting area between the respective upstanding flanges 14 defining a correspondingly generally L-shaped configuration. The foam insert 15 has an elongated cross-sectionally defined U-shaped recess at 16 within the corresponding leg and heel support portion 14 of the support base 11 with a contoured base at 17 and a recessed heel cup at 18 to fully support a patient's leg 20 and foot 21 within a heel portion 22 positioned within as illustrated generally in broken lines in FIG. 2 of the drawings.

A pair of oppositely disposed circular openings at 23 are formed in the foam insert 15 adjacent the heel cup at 18. Retention straps 24 and 25 are removably secured to the rigid base 11 opposite said foam insert 15 on said respective leg and heel support portion 12 and foot support portion 13 by multiple hook and loop fasteners F "VELCRO" brand secured respectively thereto as will be well known by those skilled in the art.

Referring to FIG. 2 of the drawings once again it will be seen that the foam insert 15 with the leg and heel support portion 12 extends substantially beyond the corresponding flanges 14 as required to support the leg 20 on three engagement sides as is required in such splint configurations. A portion 26 of the foam insert 15 within the upstanding foot portion 13 is of a reduced thickness that is required to cushion the patient's foot 21 placed thereagainst during use.

Figure 3:
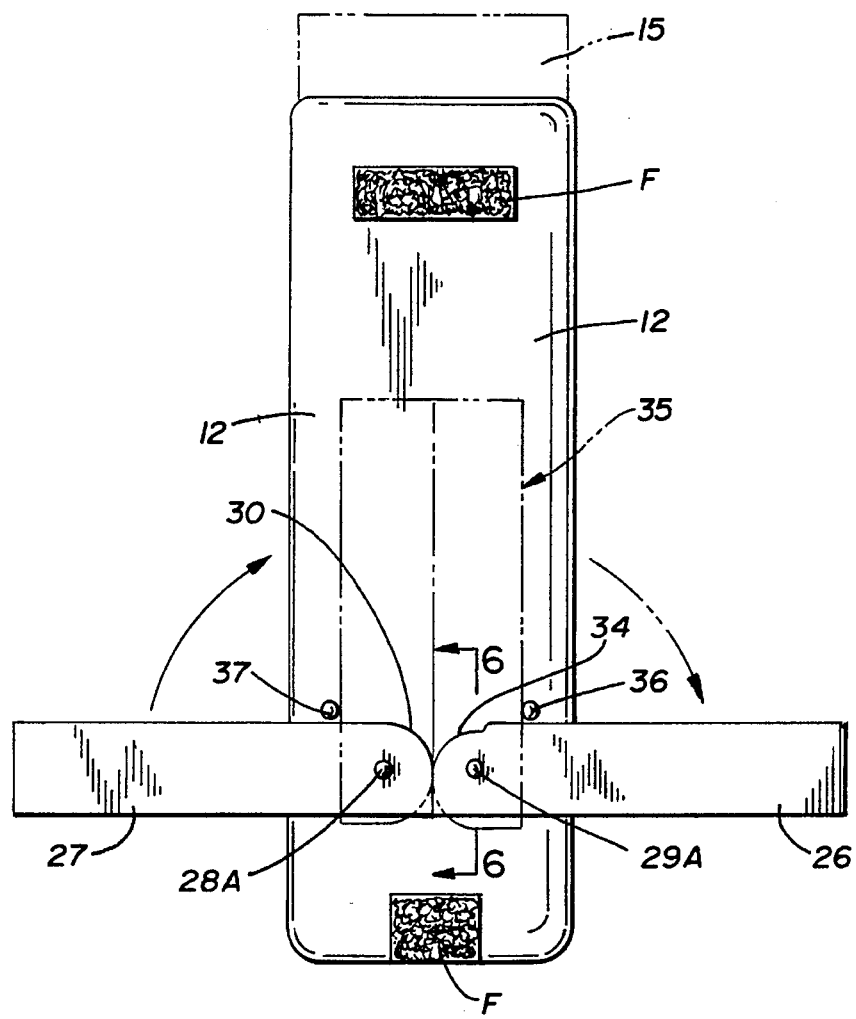
FIG. 3 is a bottom plan view of the foot splint with the straps and contoured foam insert removed for illustration purposes.
Figure 4:
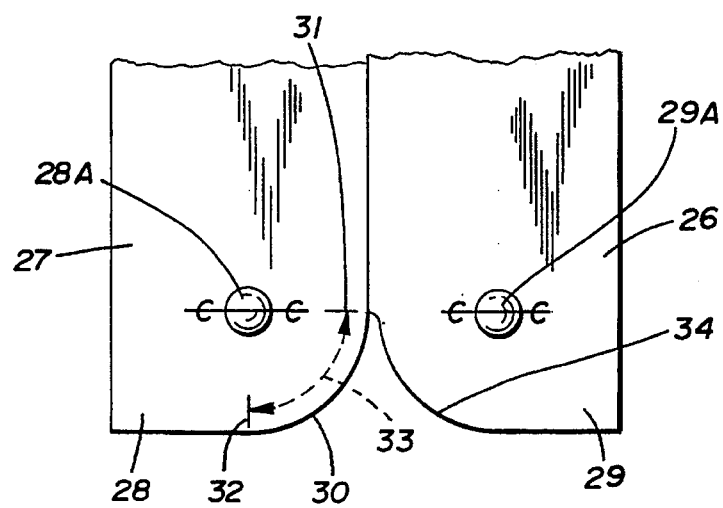
FIG. 4 is an enlarged partial bottom plan view of a portion of the pivoting stabilizers in stored position.

Referring now to FIGS. 1–3 of the drawings, a pair of movable rotational restraints 26 and 27 of the invention are pivotally secured to the leg and heel support portion 12 of the rigid base 11 inwardly from the foot portion 13. Each of the rotational restraints 26 and 27 are of a generally elongated rectangular shaped configuration with respective contoured end portions 28 and 29, with pivot pin fittings 28A and 29A therethrough in spaced horizontal aligned rotation to one another as best seen in FIG. 3 of the drawings. The rotational restraint 26 has a simple arcuate curved corner portion 30 extending between transition points 31 and 32 thereon indicated by a broken line arrow at 33 in FIG. 4 of the drawings. The rotational restraint 27 has a notched insert curved corner portion 34 so as to be in spaced relation to a true arcuate curved configuration as seen in corresponding corner portion 30.

This offset notched insert portion 34 allows for transitional clearance between the respective rotational restraints 26 and 27 during pivotal deployment from an aligned side by side storage position illustrated at 35 in broken lines in FIG. 3 of the drawings to a fully deployed outstanding position shown in solid lines in FIGS. 1, 2, and 3 of the drawings.

When deployed, the rotational restraints 26 and 27 cannot extend beyond a relative 90 degree right angle relation to said respective spaced parallel elongated flanges 14 due to the engagement of their respective end portions 28 and 29 as seen in FIG. 3 of the drawings.

Locking elements 36 and 37 extend from the surface of the leg and heel support portion 12 in spaced parallel relation to one another and are engaged by the rotation restraints 26 and 27 during and after their full deployment, locking the restraints in external position.

Figure 5:
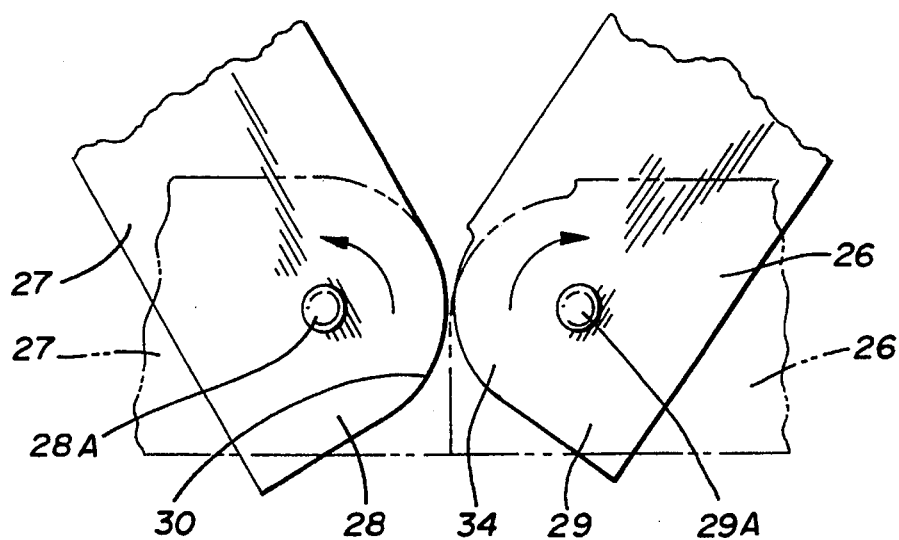
FIG. 5 is an enlarged partial plan view of the pivoting stabilizers of FIG. 4 in partially deployed relation and in fully deployed position shown in broken lines.
Figure 6:
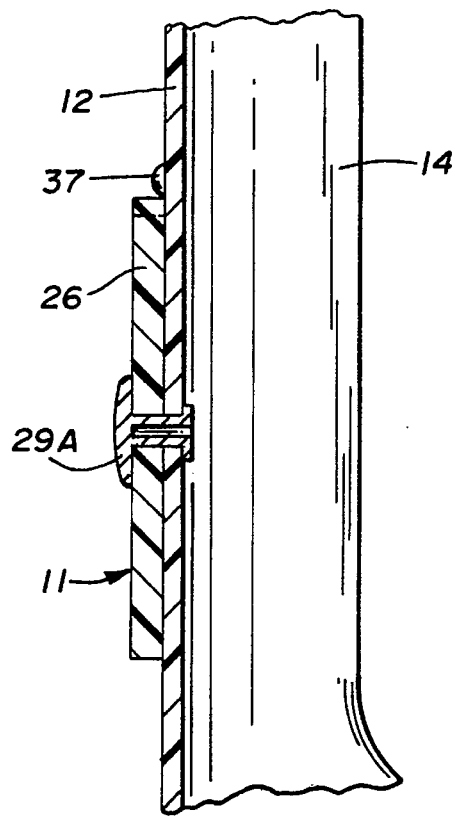
FIG. 6 is an enlarged cross-sectional view on lines 6—6 of FIG. 3.

Referring now to FIGS. 5 and 6 of the drawings an intermediate deployment position is illustrated in FIG. 5 wherein respective rotation restraints 26 and 27 are each pivoted about their respective pivot pin fittings, illustrating the required clearance therebetween achieved by the unique offset insert curved corner portion 34 on the end 29 of the rotational restraint 26.

Referring now to FIG. 6 of the drawings, the pivot pin fitting 29A and locking element 37 can be seen illustrating the pivot attachment point of the rotation restraint 26 to the base 11 as hereinbefore described.

In operation, the patient's leg and foot 20 and 21 are positioned within the foot drop splint of the invention resting on the contoured foam insert 15. The straps 24 and 25 are extended about the splint securing the leg and foot 20 and 21 within while suspending the heel 22 in spaced relation to the foam insert.

When required, the rotational restraints 26 and 27 are pivotally deployed from the base 11 extending outwardly therebeyond into a stabilizing position by engagement against one another and locking via the locking elements 36 and 37. The respective rotational restraints 26 and 27 are contoured on their respective end portions 28 and 29 so as to rotate past one another as they are deployed by use of the notched set back offset arcuate curved corner 34 and corresponding arcuate corner 30 as hereinbefore described.

Once deployed, the rotational restraints 26 and 27 prevent axial rotation of the foot and leg within the splint as will be evident to one skilled in the art.

It has thus been illustrated and described that a new and novel drop foot splint has been illustrated and described and that various changes and modifications may be made therein without departing from the spirit of the invention.

Therefore I claim:

1. A therapeutic leg and foot device comprising an L-shaped rigid support base having a leg engagement portion and a foot engagement portion, a contoured resilient synthetic insert within said support base, a pair of rotational restraints pivotally secured adjacent their distal ends to said leg engagement portion of said support base, said rotational restraints movable from a first position on said support base to a second position extending outwardly from said support base at right angles thereto, restraint straps removably positioned about said support base and said resilient synthetic insert, means for selectively securing said rotation restraints in said first position and said second position on said base, and means for interengaging said rotational restraints to one another in said first position and in said second position on said support base.

2. The therapeutic leg and foot device of claim 1 wherein said rotational restraints are of a flat elongated rectangular configuration and of a fixed length less than that of said leg engagement portion of said support base.

3. The therapeutic leg and foot device of claim 1 wherein said means for interengagement of said rotation restraints to one another in said first position and in said second position on said support base comprises, arcuate curved areas on said distal ends of said rotational restraints, said arcuate curved areas on said rotational restraints in spaced effacing relation to one another, one of said arcuate curved areas on said rotational restraints being transversely inset in relation to said other rotational restraint.

4. The therapeutic leg and foot device of claim 1 wherein said means for selectively securing said rotational restraints in said first and second position on said support base comprises locking elements on said support base in spaced relation to one another.

* * * * *